United States Patent [19]

Schwark et al.

[11] Patent Number: 5,679,712
[45] Date of Patent: Oct. 21, 1997

[54] SUBSTITUTED BENZOYLGUANIDINES, PROCESS FOR THEIR PREPARATION, THEIR USE AS A PHARMACEUTICAL OR DIAGNOSTIC, AND PHARMACEUTICAL CONTAINING THEM

[75] Inventors: Jan-Robert Schwark, Frankfurt am Main; Heinz-Werner Kleemann, Bad Homburg; Hans-Jochen Lang, Hofheim; Andreas Weichert, Frankfurt am Main; Wolfgang Scholz, Eschborn; Udo Albus, Florstadt, all of Germany

[73] Assignee: Hoechst Aktiengesellschaft, Frankfurt am Main, Germany

[21] Appl. No.: 459,966

[22] Filed: Jun. 2, 1995

Related U.S. Application Data

[63] Continuation-in-part of Ser. No. 252,786, Jun. 2, 1994, abandoned.

[51] Int. Cl.$^6$ .................. A61K 31/165; C07C 233/64
[52] U.S. Cl. .................. 514/621; 514/520; 514/521; 514/522; 514/622; 558/415; 564/162; 564/163; 564/169; 564/142
[58] Field of Search .................. 514/614, 520, 514/521, 522, 621, 622; 564/147, 162, 163, 169, 142

[56] References Cited

U.S. PATENT DOCUMENTS

| | | | |
|---|---|---|---|
| 3,780,027 | 12/1973 | Cragoe et al. | 260/239.6 |
| 5,091,394 | 2/1992 | Englert et al. | 514/331 |
| 5,292,755 | 3/1994 | Englert et al. | 514/331 |
| 5,364,868 | 11/1994 | Englert et al. | 514/331 |

FOREIGN PATENT DOCUMENTS

| | | |
|---|---|---|
| A-0416499 | 3/1991 | European Pat. Off. . |
| A-0556672 | 8/1993 | European Pat. Off. . |
| A-0556673 | 8/1993 | European Pat. Off. . |
| A-0556674 | 8/1993 | European Pat. Off. . |
| A-0612723 | 8/1994 | European Pat. Off. . |
| 1939738 | 2/1971 | Germany . |
| A-4318756 | 12/1994 | Germany . |
| 2032425 | 5/1980 | United Kingdom . |

OTHER PUBLICATIONS

English language Derwent Abstract of EP-A-612723, 1994.
English language Derwent Abstract of DE-A-4318756, 1994.
"Inhibition of Na$^+$/H$^+$ exchange suppresses nor-adrenaline release and arrhythmias in the ischemic rat heart", Schömig et al., Eur. Heart J., Book of Abstracts, 9(suppl. 1):167(1988).
"Amiloride: Antiarrhythmic and Electrophysiologic Actions in Patients With Inducible Sustained Ventricular Tachycardia", Duff et al., Circulation, 79(6):1257–1263(1989).

*Primary Examiner*—Shailendra Kumar
*Attorney, Agent, or Firm*—Finnegan, Henderson, Farabow, Garrett & Dunner, L.L.P.

[57] ABSTRACT

Benzoylguanidines of the formula I are described in which:
R(1), R(2), R(3), R(4), R(5) are as defined in the specification, and pharmaceutically tolerated salts thereof.

10 Claims, No Drawings

SUBSTITUTED BENZOYLGUANIDINES, PROCESS FOR THEIR PREPARATION, THEIR USE AS A PHARMACEUTICAL OR DIAGNOSTIC, AND PHARMACEUTICAL CONTAINING THEM

This application is a continuation-in-part of U.S. patent application Ser. No. 08/252,786 filed Jun. 2, 1994 now abandoned, which is incorporated by reference herein in its entirety.

The invention relates to benzoylguanidines of the formula I

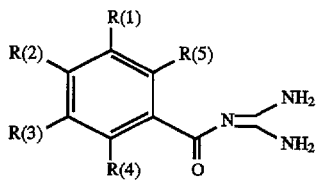

in which:
R(1) is R(6)—CO;
  R(6) being $(C_1-C_8)$-alkyl, $(C_1-C_8)$-perfluoroalkyl, $(C_3-C_8)$-alkenyl or —$C_nH_{2n}$—R(9),
    n being zero, 1, 2, 3 or 4,
    R(9) being $(C_3-C_8)$-cycloalkyl, phenyl, biphenylyl or naphthyl, where the aromatic radicals are unsubstituted or substituted by 1–3 substituents selected from the group consisting of F, Cl, $CF_3$, methyl, methoxy and NR(10)R(11);
      R(10) and R(11) being H, $(C_1-C_4)$-alkyl or $(C_1-C_4)$-perfluoroalkyl;
R(2) is H, F, Cl, Br, I, OH, CN, $NO_2$, $(C_1-C_8)$-alkyl, $(C_1-C_8)$-perfluoroalkyl, $(C_3-C_8)$-alkenyl or —$C_nH_{2n}$R(15);
  n being zero, 1, 2, 3 or 4;
  R(15) being $(C_3-C_8)$-cycloalkyl, phenyl, biphenylyl or naphthyl, where the aromatic radicals are unsubstituted or substituted by 1–3 substituents selected from the group consisting of F, Cl, $CF_3$, methyl, methoxy and NR(16)R(17);
    R(16) and R(17) being H, $(C_1-C_4)$-alkyl or $(C_1-C_4)$-perfluoroalkyl;
or
R(2) is $(C_1-C_9)$-heteroaryl, which is linked via C or N and which is unsubstituted or substituted by 1–3 substituents selected from the group consisting of F, Cl, $CF_3$, $CH_3$, methoxy, hydroxyl, amino, methylamino and dimethylamino;
or
R(2) is SR(18), —OR(18), —NR(18)R(19) or —CR(18)R(19)R(20);
  R(18) is —$C_aH_{2a}$—$(C_1-C_9)$-heteroaryl, which is unsubstituted or substituted by 1–3 substituents selected from the group consisting of F, Cl, $CF_3$, $CH_3$, methoxy, hydroxyl, amino, methylamino or dimethylamino;
    a is zero, 1 or 2;
  R(19) and R(20) independently of each other, are defined as R(18) or are hydrogen, $(C_1-C_4)$-alkyl or $(C_1-C_4)$-perfluoroalkyl;
or
R(2) is R(21)—$SO_m$ or R(22)R(23)N—$SO_2$—;
  m being 1 or 2;
  R(21) being $(C_1-C_8)$-alkyl, $(C_1-C_8)$-perfluoroalkyl, $(C_3-C_8)$-alkenyl or —$C_nH_{2n}$—R(24);
    n being zero, 1, 2, 3 or 4;
    R(24) being $(C_3-C_8)$-cycloalkyl, phenyl, biphenylyl or naphthyl; where the aromatic radicals are unsubstituted or substituted by 1–3 substituents selected from the group consisting of F, Cl, $CF_3$, methyl, methoxy and NR(27)R(28);
      R(27) and R(28) being H, $(C_1-C_4)$-alkyl or $(C_1-C_4)$-perfluoroalkyl;
  R(22) being H, $(C_1-C_8)$-alkyl, $(C_1-C_8)$-perfluoroalkyl, $(C_3-C_8)$-alkenyl or —$C_nH_{2n}$—R(29),
    n being zero, 1, 2, 3 or 4;
    R(29) being $(C_3-C_8)$-cycloalkyl, phenyl, biphenylyl or naphthyl, where the aromatic radicals are unsubstituted or substituted by 1–3 substituents selected from the group consisting of F, Cl, $CF_3$, methyl, methoxy and NR(30)R(31);
      R(30) and R(31) being H, $(C_1-C_4)$-alkyl or $(C_1-C_4)$-perfluoroalkyl;
  R(23) being H, $(C_1-C_4)$-alkyl or $(C_1-C_4)$-perfluoroalkyl;
or
  R(22) and R(23) together can be 4 or 5 methylene groups of which one $CH_2$ group can be replaced by oxygen, S, NH, N—$CH_3$ or N-benzyl;
or
R(2) is R(33)X—;
  X is oxygen, S, NR(34) or (D=O)A—;
  A being oxygen or NR(34);
  D being C or SO;
  R(33) being $(C_1-C_8)$-alkyl, $(C_3-C_8)$-alkenyl, $(CH_2)_bC_dF_{2d+1}$ or —$C_nH_{2n}$—R(36);
    b is zero or 1;
    d is 1, 2, 3, 4, 5, 6 or 7;
    n is zero, 1, 2, 3 or 4;
    R(36) is $(C_3-C_8)$-cycloalkyl, phenyl, biphenylyl or naphthyl, where the aromatic radicals are unsubstituted or substituted by 1–3 substituents selected from the group consisting of F, Cl, $CF_3$, methyl, methoxy and NR(37)R(38);
      R(37) and R(38) being H, $(C_1-C_4)$-alkyl or $(C_1-C_4)$-perfluoroalkyl;
    R(34) being H, $CH_3$ or $CF_3$;
or
R(2) is —SR(40), —OR(40), —NHR(40), —NR(40)R(41), —CHR(40)R(42), —[CR(42)R(43)OH], —C≡CR(45), —CR(46)=CR(45) or —[CR(47) R(48)]$_u$—(CO)—[CR(49)R(50)]$_v$—R(44);
  R(40) and R(41) are identical or different and are —$(CH_2)_p$—$(CHOH)_q$—$(CH_2)_r$—$(CHOH)_r$R(51) or —$(CH_2)_p$—O—$(CH_2$—$CH_2O)_q$—R(51);
    R(51) is hydrogen or methyl;
    u is 1, 2, 3 or 4;
    v is zero, 1, 2, 3 or 4;
    p, q and r are identical or different and are zero, 1, 2, 3 or 4;
  t is 1, 2, 3 or 4;
  R(42) and R(43) are identical or different and are hydrogen or $(C_1-C_6)$-alkyl or, together with the carbon atom carrying them, form a $(C_3-C_8)$-cycloalkyl;
  R(44) is H, $(C_1-C_6)$-alkyl, $(C_3-C_8)$-cycloalkyl or —$C_eH_{2e}$—R(45);
    e being zero, 1, 2, 3 or 4;
  R(45) is phenyl, which is unsubstituted or substituted by 1–3 substituents selected from the group consisting of F, Cl, $CF_3$, methyl, methoxy and NR(52)R(53);
    R(52) and R(53) being H or $(C_1-C_4)$-alkyl;
or R(45) is $(C_1-C_9)$-heteroaryl, which is unsubstituted or substituted as phenyl;

or

R(45) is $(C_1-C_6)$-alkyl which is unsubstituted or substituted by 1-3 OH;

R(46), R(47), R(48), R(49) and R(50) are hydrogen or methyl;

R(3) is defined as R(1) or R(2);

R(4) and R(5) are, independently of each other, defined as R(2);

and pharmaceutically tolerated salts thereof.

Compounds of the formula I are preferred in which:

R(1) is R(6)—CO;

R(6) being $(C_1-C_8)$-alkyl, $CF_3$ or —$C_nH_{2n}$—R(9);

n being zero, 1, 2, 3 or 4;

R(9) being $(C_3-C_8)$-cycloalkyl or phenyl, where phenyl is unsubstituted or substituted by 1–3 substituents selected from the group consisting of F, Cl, $CF_3$, methyl, methoxy and NR(10)R(11);

R(10) and R(11) being H or $CH_3$;

R(2) is H, F, Cl, Br, I, OH, CN, $(C_1-C_8)$-alkyl, $CF_3$, $(C_3-C_8)$-alkenyl or —$C_nH_{2n}$R(15);

n being zero, 1, 2, 3 or 4;

R(15) being $(C_3-C_8)$-cycloalkyl or phenyl, where phenyl is unsubstituted or substituted by 1–3 substituents selected from the group consisting of F, Cl, $CF_3$, methyl, methoxy and NR(16)R(17);

R(16) and R(17) being H or $CH_3$;

or

R(2) is $(C_1-C_9)$-heteroaryl, which is linked via C or N and which is unsubstituted or substituted by 1–3 substituents selected from the group consisting of F, Cl, $CF_3$, $CH_3$, methoxy, hydroxyl, amino, methylamino and dimethylamino;

or

R(2) is SR(18) or —OR(18);

R(18) is —$C_aH_{2a}$—$(C_1-C_9)$-heteroaryl, which is unsubstituted or substituted by 1–3 substituents selected from the group consisting of F, Cl, $CF_3$, $CH_3$, methoxy, hydroxyl, amino, methylamino or dimethylamino;

a is zero, 1 or 2;

or

R(2) is R(21)—$SO_m$;

m being 2;

R(21) being $(C_1-C_8)$-alkyl, $CF_3$, $(C_3-C_8)$-alkenyl or —$C_nH_{2n}$—R(24);

n being zero, 1, 2, 3 or 4;

R(24) being $(C_3-C_8)$-cycloalkyl or phenyl, which is unsubstituted or substituted by 1–3 substituents selected from the group consisting of F, Cl, $CF_3$, methyl, methoxy and NR(27)R(28);

R(27) and R(28) being H or $CH_3$;

or

R(2) is R(33)X—;

X is oxygen, S, NR(34) or (C=O)A—;

A being oxygen or NR(34);

R(33) being $(C_1-C_8)$-alkyl, $(CH_2)_bC_dF_{2d+1}$ or —$C_nH_{2n}$—R(36);

b is zero or 1;

d is 1, 2, 3, 4, 5, 6 or 7;

n is zero or 1;

R(36) is $(C_3-C_8)$-cycloalkyl or phenyl, which is unsubstituted or substituted by 1–3 substituents selected from the group consisting of F, Cl, $CF_3$, methyl, methoxy and NR(37)R(38);

R(37) and R(38) being H or $CH_3$;

R(34) being H or $CH_3$;

R(3) is defined as R(1) or R(2);

R(4) and R(5) are, independently of each other, defined as R(2), and pharmaceutically tolerated salts thereof.

Compounds of the formula I are particularly preferred in which:

R(1) is R(6)—CO;

R(6) being $(C_1-C_8)$-alkyl, $CF_3$ or —$C_nH_{2n}$—R(9);

n being zero;

R(9) being $(C_3-C_8)$-cycloalkyl or phenyl, where phenyl is unsubstituted or substituted by 1–3 substituents selected from the group consisting of F, Cl, $CF_3$, methyl, methoxy and NR(10)R(11);

R(10) and R(11) being H or $CH_3$;

R(2) is H, F, Cl, Br, I, OH, CN, $(C_1-C_8)$-alkyl, $CF_3$ or —$C_nH_{2n}$R(15);

n being zero, 1 or 2;

R(15) being $(C_3-C_8)$-cycloalkyl or phenyl, where phenyl is unsubstituted or substituted by 1–3 substituents selected from the group consisting of F, Cl, $CF_3$, methyl, methoxy and NR(16)R(17);

R(16) and R(17) being H or $CH_3$;

or

R(2) is quinolyl, isoquinolyl, pyrrolyl, pyridyl or imidazolyl, which are linked via C or N and which are unsubstituted or substituted by 1–3 substituents selected from the group consisting of F, Cl, $CF_3$, $CH_3$, methoxy, hydroxyl, amino, methylamino and dimethylamino;

or

R(2) is SR(18) or —OR(18);

R(18) is quinolyl, isoquinolyl, pyrrolyl or $(CH_2)_{0-1}$-pyridyl, which are linked via C or N and which are unsubstituted or substituted by 1–3 substituents selected from the group consisting of F, Cl, $CF_3$, $CH_3$, methoxy, hydroxyl, amino, methylamino or dimethylamino;

or

R(2) is R(33)X—;

X is oxygen, S or NR(34);

R(33) is $(C_1-C_8)$-alkyl, $(CH_2)_bC_dF_{2d+1}$ or —$C_nH_{2n}$—R(36);

b is zero or 1;

d is 1, 2, 3 or 4;

n is zero or 1;

R(36) is phenyl, which is unsubstituted or substituted by 1–3 substituents selected from the group consisting of F, Cl, $CF_3$, methyl, methoxy and NR(37)R(38);

R(37) and R(38) being H or $CH_3$;

R(34) being $CH_3$;

R(3) is defined as R(1) or is H, F, Cl, Br, I, OH, $(C_1-C_8)$-alkyl, $CF_3$ or —$C_nH_{2n}$R(15);

n being zero, 1 or 2;

R(15) being $(C_3-C_8)$-cycloalkyl or phenyl, which is unsubstituted or substituted by 1–3 substituents selected from the group consisting of F, Cl, $CF_3$, methyl, methoxy and NR(16)R(17);

R(16) and R(17) being H or $CH_3$;

or

R(3) is quinolyl, isoquinolyl, pyrrolyl, pyridyl or imidazolyl, which are linked via C or N and which are unsubstituted or substituted by 1–3 substituents selected from the group consisting of F, Cl, $CF_3$, $CH_3$, methoxy, hydroxyl, amino, methylamino and dimethylamino;

or

R(3) is R(21)—SO$_m$;

m being 2;

R(21) being (C$_1$-C$_4$)-alkyl or CF$_3$;

R(4) and R(5) are, independently of each other, hydrogen, F, Cl, OH, CH$_3$, CF$_3$, OMe, OCF$_3$, OH or NH$_2$;

and pharmaceutically tolerable salts thereof.

Compounds are very especially preferred in which:

R(1) is R(6)—CO;

R(6) being (C$_1$-C$_2$)-alkyl or —C$_n$H$_{2n}$—R(9);

n being zero;

R(9) being phenyl, where phenyl is unsubstituted or substituted by 1–3 substituents selected from the group consisting of F, Cl, CF$_3$, methyl, methoxy and NR(10)R(11);

R(10) and R(11) being H or CH$_3$;

R(2) is H, F, Cl, Br, I, OH, (C$_1$-C$_8$)-alkyl or —C$_n$H$_{2n}$R(15);

n being zero, 1 or 2;

R(15) being (C$_3$-C$_8$)-cycloalkyl or phenyl, where phenyl is unsubstituted or substituted by 1–3 substituents selected from the group consisting of F, Cl, CF$_3$, methyl, methoxy and NR(16)R(17);

R(16) and R(17) being H or CH$_3$;

or

R(2) is quinolyl, isoquinolyl, pyrrolyl, pyridyl or imidazolyl, which are linked via C or N and which are unsubstituted or substituted by 1–3 substituents selected from the group consisting of F, Cl, CF$_3$, CH$_3$, methoxy, hydroxyl, amino, methylamino and dimethylamino;

or

R(2) is SR(18) or —OR(18);

R(18) is quinolyl, isoquinolyl, pyrrolyl or (CH$_2$)$_{0-1}$-pyridyl, which are linked via C or N and which are unsubstituted or substituted by 1–3 substituents selected from the group consisting of F, Cl, CF$_3$, CH$_3$, methoxy, hydroxyl, amino, methylamino or dimethylamino;

or

R(2) is R(33)X—;

X is oxygen;

R(33) is (C$_1$-C$_6$)-alkyl or —C$_n$H$_{2n}$—R(36);

n is zero or 1;

R(36) is phenyl, which is unsubstituted or substituted by 1–3 substituents selected from the group consisting of F, Cl, CF$_3$, methyl, methoxy and NR(37)R(38);

R(37) and R(38) being H or CH$_3$;

R(3) is H, F, Cl, Br, I or —C$_n$H$_{2n}$R(15);

n being zero, 1 or 2;

R(15) being (C$_3$-C$_8$)-cycloalkyl or phenyl, which is unsubstituted or substituted by 1–3 substituents selected from the group consisting of F, Cl, CF$_3$, methyl, methoxy and NR(16)R(17);

R(16) and R(17) being H or CH$_3$;

or

R(3) is R(21)—SO$_m$;

m being 2;

R(21) being (C$_1$-C$_4$)-alkyl;

R(4) and R(5) are, independently of each other, hydrogen, F, Cl, OH, CH$_3$, CF$_3$, OMe, OCF$_3$, OH or NH$_2$;

and pharmaceutically tolerable salts thereof.

(C$_1$-C$_9$)-Heteroaryl is to be understood as meaning, in particular, radicals which are derived from phenyl or naphthyl and in which one or more CH groups are replaced by N and/or in which at least two adjacent CH groups (while forming a five-membered aromatic ring) are replaced by S, NH or O. Moreover, it is also possible for one or both atoms of the condensation site of bicyclic radicals (as in indolizinyl) to be N atoms.

Heteroaryl means, in particular, furanyl, thienyl, pyrrolyl, imidazolyl, pyrazolyl, triazolyl, tetrazolyl, oxazolyl, isoxazolyl, thiazolyl, isothiazolyl, pyridyl, pyrazinyl, pyrimidinyl, pyridazinyl, indolyl, indazolyl, quinolyl, isoquinolyl, phthalazinyl, quinoxalinyl, quinazolinyl or cinnolinyl.

If one of the substituents R(1) to R(60) contains one or more asymmetric centers, they can have either the S or the R configuration. The compounds can exist as optical isomers, diastereomers, racemates or mixtures of these.

The alkyl radicals which have been mentioned can be straight-chain or branched.

The invention furthermore relates to a process for the preparation of the compound I, which comprises reacting compounds of the formula II

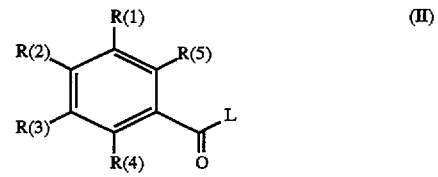

with guanidine, R(1) to R(5) having the abovementioned meaning and L being a leaving group which can readily be substituted by a nucleophile.

The activated acid derivatives of the formula II, in which L is an alkoxy group, preferably a methoxy group, a phenoxy group, a phenylthio, methylthio or 2-pyridylthio group, or a nitrogen heterocycle, preferably 1-imidazolyl, are obtained advantageously in a manner known per se from the carbonyl chlorides (formula II, L=Cl) on which they are based and which, in turn, can be prepared in a manner known per se from the carboxylic acids (formula II, L=OH) on which they are based, for example thionyl chloride.

In addition to the carbonyl chlorides of the formula II (L=Cl), other activated acid derivatives of the formula II can also be prepared, in a manner known per se, directly from the benzoic acid derivatives (formula II, L=OH) on which they are based, for example the methyl esters of the formula II where L=OCH$_3$ by treatment with gaseous HCl in methanol, the imidazolides of the formula II by treatment with carbonyldiimidazole [L=1-imidazolyl, Staab, Angew. Chem. Int. Ed. Engl. 1, 351–367 (1962)], the mixed anhydrides II with Cl-COOC$_2$H$_5$ or tosyl chloride in the presence of triethylamine in an inert solvent, and benzoic acids can be activated with dicyclohexylcarbodiimide (DCC) or with O-[(cyano(ethoxycarbonyl)methylene)amino]-1,1,3,3-tetramethyluronium tetrafluoroborate ("TOTU") [Proceedings of the 21. European Peptide Symposium, Peptides 1990, Editors E. Giralt and D. Andreu, Escom, Leiden, 1991]. A series of suitable methods for the preparation of activated carboxylic acid derivatives of the formula II can be found in J. March, Advanced Organic Chemistry, Third Edition (John Wiley & Sons, 1985), p. 350, where the source references are cited.

An activated carboxylic acid derivative of the formula II is reacted with guanidine in a manner known per se in a protic or aprotic polar, but inert, organic solvent. Methanol, isopropanol or THF have proven themselves in the reaction of the methyl benzoates (11, L=OMe) with guanidine, the temperatures being 20° C. to the boiling point of these solvents. In most reactions of compounds II with salt-free guanidine, the process was advantageously carried out in aprotic inert solvents, such as THF, dimethoxyethane or dioxane. Water, together with a base, such as, for example, NaOH, can also be used as solvent in the reaction of II with guanidine.

If L=Cl, the process is carried out advantageously with the addition of an acid scavenger, for example in the form of excess guanidine, to bind the hydrohalic acid.

Some of the basic benzoic acid derivatives of the formula II are known and described in the literature. The unknown compounds of the formula II can be prepared by methods known from the literature. The benzoic acids obtained are reacted by one of the above-described process variants to give compounds I according to the invention.

Some substituents can successfully be introduced into the 3-, 4- and 5-position by methods which are known from the literature, namely palladium-mediated cross coupling of aryl halides or aryl triflates with, for example, organostannanes, organoboric acids or organoboranes, or organocopper or organozinc compounds.

In general, benzoylguanidines are weak bases and can bind acid with the formation of salts. Suitable acid addition salts are salts of all pharmacologically acceptable acids, for example halides, in particular hydrochlorides, lactates, sulfates, citrates, tartrates, acetates, phosphates, methylsulfonates and p-toluenesulfonates.

The compounds I are substituted acylguanidines.

The best-known representative of the acylguanidines is the pyrazine derivative amiloride, which is used in therapy as a potassium-sparing diuretic. A large number of other amiloride-type compounds are described in the literature, for example dimethylamiloride or ethylisopropylamiloride.

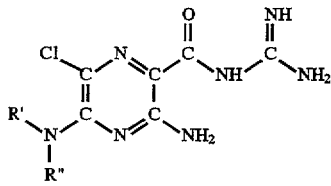

Amiloride: R', R"=H
Dimethylamiloride: R', R"=CH,
Ethylisopropylamiloride: R'=$C_2H_5$, R"=CH($CH_3$)$_2$ Moreover, tests are known which suggest that amiloride has antiarrhythmic properties (Circulation 79, 1257–63 (1989)). However, its broad use as an antiarrhythmic is restricted by the fact that this effect is only weakly pronounced and is accompanied by a hypotensive and saluretic activity, and these side effects are undesired in the treatment of cardiac arrhythmias.

Experiments on isolated animal hearts have also suggested that amiloride has antiarrhythmic properties (Eur. Heart J. 9 (suppl. 1): 167 (1988) (book of abstracts)). For example, it has been found on rats' hearts that artificially induced ventricular fibrillation can be suppressed completely by amiloride. In this model, the abovementioned amiloride derivative ethylisopropylamiloride was even more potent than amiloride itself.

U.S. Pat. No. 5,091,394 (HOE 89/F 288) describes benzoylguanidines which carry a hydrogen atom in the position which corresponds to the radical R(1). German Patent Application P 42 04 575.4 (HOE 92/F 034), now U.S. Pat. No. 5,373,024 proposes benzoylguanidines in which, however, the substituents do not have the meanings claimed in the present invention.

U.S. Pat. No. 3,780,027 claims acylguanidines whose structure is similar to those of the compounds I and which are derived from commercially available loop diuretics, such as bumetanide. Accordingly, a powerful salidiuretic activity of these compounds is reported.

It was therefore surprising that the compounds according to the invention have no undesired, disadvantageous salidiuretic properties, but have a very good activity against arrhythmias as they occur, for example, in connection with oxygen deficiencies. Due to their pharmacological properties, the compounds are highly suitable for use as antiarrhythmics with a cardioprotective component for the prophylaxis and treatment of cardiac infarctions and for the treatment of angina pectoris, in which context they also preventively inhibit, or reduce greatly, the pathophysiological processes in the formation of ischemia-induced damage, in particular when ischemia-induced cardiac arrhythmias are triggered. Due to inhibition of the cellular $Na^+/H^+$ exchange mechanism, the compounds of the formula I according to the invention, which have a protective activity against pathological hypoxic and ischemic situations, can be used as pharmaceuticals for the treatment of all acute or chronic damage triggered by ischemia or for the treatment of directly or collaterally induced diseases. This applies to their use as pharmaceuticals for surgical interventions, for example in connection with organ transplants, where the compounds can be used for the protection of the organs in the donor before and during their removal, for the protection of removed organs, for example in their treatment with, or storage in, physiological bathing fluids, and for the transfer into the recipient organism. Equally, the compounds are valuable protective pharmaceuticals when angioplastic surgical interventions are carried out, for example on the heart or on peripheral blood vessels. In correspondence with their protective activity against ischemia-induced damage, the compounds are also suitable as pharmaceuticals for the treatment of ischemias of the nervous system, in particular of the central nervous system, where they are suitable, for example, for the treatment of stroke or of brain edema. Moreover, the compounds of the formula I according to the invention are also suitable for the treatment of forms of shock, for example allergic, cardiogenic, hypovolemic and bacterial shock.

Moreover, the compounds of the formula I according to the invention are distinguished by a powerful inhibitory action on cell proliferation, for example fibroblast cell proliferation and proliferation of the smooth vascular muscle cells. This is why the compounds of the formula I are suitable as valuable therapeutic agents for diseases in which cell proliferation is a direct or collateral cause, and they can therefore be used as antiatherosclerotics, agents against diabetic late complications, cancers, fibrotic disorders, such as pulmonary fibrosis, hepatic fibrosis or renal fibrosis, organ hypertrophies and hyperplasias, in particular in prostatic hyperplasia or prostatic hypertrophy.

The compounds according to the invention are valuable inhibitors of the cellular sodium/proton antiporter ($Na^+/H^+$ exchanger), which is elevated in a large number of diseases (essential hypertension, atherosclerosis, diabetes and the like) even in those cells which are readily accessible to measurements, such as in erythrocytes, thrombocytes or leucocytes. The compounds according to the invention are therefore suitable as outstanding and simple scientific tools, for example in their use as diagnostics for determining, and distinguishing between, particular forms of hypertension, and also of atherosclerosis, diabetes, proliferative disorders and the like. Moreover, the compounds of the formula I are suitable for preventive therapy for preventing the genesis of hypertension, for example of essential hypertension.

In contrast to the known compounds, the solubility in water of the compounds according to the invention is significantly improved. They are therefore much better suited to intravenous administration.

Pharmaceuticals which contain a compound I can be administered orally, parenterally, intravenously, rectally or by inhaling, the preferred way of administration depending on the particular symptom of the disease. The compounds I can be used by themselves or together with pharmaceutical auxiliaries, and they can be employed both in veterinary medicine and human medicine.

A person skilled in the art knows, on the basis of his expert knowledge, which auxiliaries are suitable for the desired pharmaceutical formulation. Auxiliaries which can be used in addition to solvents, gel formers, bases for suppositories, tableting auxiliaries, and other excipients for active substances are, for example, antioxidants, dispersants, emulsifiers, antifoams, flavor improvers, preservatives, solubilizers or colorants.

For an oral dosage form, the active compounds together with the suitable additives, such as carriers, stabilizers or inert diluents, are mixed and formulated by customary methods to give suitable dosage forms, such as tablets, sugar-coated tablets, hard gelatin capsules, or aqueous, alcoholic or oily solutions. Inert excipients which can be used are, for example, gum arabic, magnesia, magnesium carbonate, potassium phosphate, lactose, glucose or starch, in particular corn starch. Dry granules or moist granules can be used for the preparation. Examples of oily carriers or examples of solvents are vegetable or animal oils, such as sunflower oil or cod liver oil.

For subcutaneous or intravenous administration, the active compounds, if desired together with the substances which are customary for this purpose, such as solubilizers, emulsifiers or other auxiliaries, are dissolved, suspended or emulsified. Examples of suitable solvents are: water, physiological saline or alcohols, for example ethanol, propanol, glycerol, and also sugar solutions, such as glucose or mannitol solutions, or else a mixture of the various solvents which have been mentioned above.

Pharmaceutical formulations which are suitable for administration in the form of aerosols or sprays are, for example, solutions, suspensions or emulsions of the active substance of the formula I in a pharmaceutically acceptable solvent, such as, in particular, ethanol or water, or else in a mixture of such solvents.

If required, the formulation can also contain other pharmaceutical auxiliaries, such as surfactants, emulsifiers and stabilizers, and a propellent gas. The concentration of active substance in such a preparation is generally from about 0.1 to 10, in particular from about 0.3 to 3% by weight.

The dose of the active substance of the formula I to be administered and the frequency of administration will depend on the power and duration of action of the compounds used; in addition also on the nature and severity of the disease to be treated and on the sex, age, weight and individual responsiveness of the mammal to be treated.

On average, the daily dosage rate of a compound of the formula I in the case of a patient of approximately 75 kg will be at least 0.001 mg/kg, preferably 0.01 mg/kg, up to not more than 10 mg/kg, preferably 1 mg/kg, of body weight. If the disease is acute, such as immediately after suffering a cardiac infarction, even higher and, in particular, more frequent, doses may be required, for example up to 4 single doses per day. In particular, for intravenous administration, such as in the case of a patient who has suffered an infarction and is under intensive care, up to 200 mg per day may be required.

List of abbreviations

| | |
|---|---|
| MeOH | methanol |
| DMF | N,N-dimethylformamide |
| EI | electron impact |
| DCI | desorption-chemical ionization |
| RT | room temperature |
| EA | ethyl acetate (EtOAc) |
| mp | melting point |
| HEP | n-heptane |
| ES | electron spray |
| FAB | fast atom bombardment |
| $CH_2Cl_2$ | dichloromethane |
| THF | tetrahydrofuran |
| eq. | equivalent |
| mol % | mol percent |
| (dppf) | 1,1-bis(diphenylphosphino)ferrocene |
| AIBN | azobisisobutyronitrile |

Experimental part

General instructions for preparing benzoylguanidines (I)
Variant A: from benzoic acids (11, L=OH)

1.0 eq. of the benzoic acid derivative of the formula II is dissolved or suspended in anhydrous THF (5 ml/mmol) and 1.1 eq. of carbonyldiimidazole are then added. After stirring at RT for 2 hours, 5.0 eq. of guanidine are introduced into the reaction solution. After stirring overnight, the THF is distilled off under reduced pressure (rotary evaporator), water is added, the pH is adjusted to from 6 to 7 with 2N HCl and the corresponding benzoylguanidine (formula I) is filtered off. The benzoylguanidines thus obtained can be converted into the corresponding salts by treatment with aqueous, methanolic or ethereal hydrochloric acid or other pharmacologically tolerated acids.

General instructions for preparing benzoylguanidines (I)
Variant B: from alkyl esters of benzoic acid (11, L=O-alkyl)

1.0 ,eq. of the benzoic acid alkyl ester of the formula II and 5.0 eq. of guanidine (free base) are dissolved in isopropanol or suspended in THF and boiled under reflux (typical reaction time, 2 to 5 h) until transformation is complete (monitoring by thin layer chromatography). The solvent is distilled off under reduced pressure (rotary evaporator), and the residue is taken up in EE and washed 3× with $NaHCO_3$ solution. Drying then takes place over $Na_2SO_4$, the solvent is distilled off in vacuo, and chromatography takes place on silica gel using a suitable eluent, e.g. EA/MeOH 5:1. (Salt formation, compare Variant A)

Example 1: 3-Acetyl-4-hydroxybenzoylguanidine

1a)

4-Acetoxybenzoic acid was converted by Fries displacement, with 3 eq. of $AlCl_3$ at 140° C., into 3-acetyl-4-hydroxybenzoic acid.

1b)

1.0 eq. of 3-acetyl-4-hydroxybenzoic acid was reacted in accordance with Variant A with 1.1 eq. of carbonyldiimidazole and 5 eq. of guanidine. Colorless crystals, mp 218°–221° C.

Example 2: 3-Acetyl-4-methoxybenzoylguanidine hydrochloride

2a)

1.0 eq. of 3-acetyl-4-hydroxybenzoic acid [preparation, see 1a)] was reacted with 2.2 eq. each of $K_2CO_3$ and methyl iodide in absolute acetone to form methyl 3-acetyl-4-methoxybenzoate. Colorless crystals, mp 54°–58° C.

2b)

The ester from 2a) was reacted with guanidine in accordance with Variant B. Colorless crystals, mp 156°–162° C. The hydrochloride was prepared in accordance with Variant A. Colorless crystals, mp 206°–212° C.

Example 3: 3-Acetyl-4-isopropoxybenzoylguanidine hydrochloride

3a)

1.0 eq. of 3-acetyl-4-hydroxybenzoic acid was reacted with 2.2 eq. each of $K_2CO_3$ and isopropyl bromide in absolute DMF to form isopropyl 3-acetyl-4-isopropoxybenzoate. Yellowish oil, MS (ES): 265 (M+1).

3b)

The ester from 3a) was reacted with guanidine in accordance with Variant B and converted into the hydrochloride. Colorless crystals, mp 158°–170° C.

Example 4: 3-Acetyl-4-benzyloxybenzoylguanidine hydrochloride

4a)

1.0 eq. of methyl 3-acetyl-4-hydroxybenzoate was reacted with 1.1 eq. each of $K_2CO_3$ and benzyl bromide in absolute DMF to form methyl 3-acetyl-4-benzyloxybenzoate. Colorless crystals, mp 68°–72° C.

4b)

The ester from 4a) was reacted with guanidine in accordance with Variant B and isolated as the hydrochloride. Colorless crystals, mp 175°–182° C.

Example 5: 3-Acetyl-5-bromo-4-hydroxybenzoylguanidine hydrochloride

Methyl 3-acetyl-5-bromo-4-hydroxybenzoate, which is known from the literature, was converted into the benzoylguanidine in accordance with Variant B and isolated as the hydrochloride. Colorless crystals, mp 230° C. (with decomposition).

Example 6: 3-Acetylbenzoylguanidine hydrochloride 1.0 eq. of 3-acetylbenzoic acid was reacted in accordance with Variant A with 1.1 eq. of carbonyldiimidazole and 5 eq. of guanidine, and isolated as the hydrochloride. Colorless crystals, mp 202°–204° C.

Example 7: 3-Benzoylbenzoylguanidine hydrochloride 1.0 eq. of 3-benzoylbenzoic acid was reacted in accordance with Variant A with 1.1 eq. of carbonyldiimidazole and 5 eq. of guanidine, and isolated as the hydrochloride. Colorless crystals, mp 150°–154° C.

Example 8: 3-Acetyl-4-isopropylbenzoylguanidine hydrochloride

8a)

Methyl 3-acetyl-4-hydroxybenzoate was converted, in $CH_2Cl_2$, into the 4-triflate using pyridine and trifluoromethanesulfonic anhydride. Yellowish oil, MS (ES): 327 (M+1).

8b)

1.0 eq. of the triflate from 8a) was dissolved in THF and 3 mol % of $PdCl_2$ (dppf) and 4 mol % of copper(I) iodide were added. 1.5 eq. of isopropyl/zinc chloride (prepared from the Grignard reagent and zinc chloride) were added to this suspension, which was stirred at RT. Standard working up with 1N HCl yielded, after working up by column chromatography, methyl 3-acetyl-4-isopropylbenzoate. Oil, MS (ES): 221 (M+1).

8c)

The methyl benzoate derivative from 8b) was hydrolyzed under standard conditions (MeOH/NaOH), and the resulting benzoic acid was converted into the guanidide in accordance with Variant A, and isolated as the hydrochloride. Colorless crystals, mp 107°–118° C.

Example 9: 3-Acetyl-4-isobutylbenzoylguanidine hydrochloride

Was prepared in analogy with Example 8. Colorless crystals, mp 124°–130° C.

Example 10: 3-Acetyl-4-cyclopentylbenzoylguanidine hydrochloride

Was prepared in analogy with Example 8. Colorless crystals, mp 148°–154° C.

Example 11: 3-Acetyl-4-(2,2-dimethylpropyl) benzoylguanidine hydrochloride

Was prepared in analogy with Example 8. Colorless crystals, mp 138°–148° C.

Example 12: 3-Acetyl-4-fluorobenzoylguanidine hydrochloride

12a)

In accordance with a method known from the literature, methyl 3-bromo-4-fluorobenzoate is reacted, under $(Ph_3P)_2PdCl_2$ catalysis, with (trimethylsilyl)acetylene to form methyl 4-fluoro-3-(2-trimethylsilylethinyl)benzoate. MS (ES): 251 (M+1).

12b)

The product from 12a) is reacted, in 90% acetic acid and in the presence of concentrated sulfuric acid, with mercuric acetate to form methyl 3-acetyl-4-fluorobenzoate. MS (ES): 198 (M+1).

12c)

The methyl benzoate derivative from 12b) was hydrolyzed under standard conditions (MeOH/NaOH) and the resulting benzoic acid converted into the guanidide in accordance with Variant A and isolated as the hydrochloride. Colorless crystals, mp 178°–185° C.

Example 13: 3-Acetyl-4-imidazolylbenzoylguanidine hydrochloride 1.0 eq. of 3-acetyl-4-fluorobenzoylguanidine hydrochloride was reacted, in DMF and in the presence of 1.1 eq. of $K_2CO_3$, with 2 eq. of imidazole to form the 4-imidazolyl derivative, and isolated as the hydrochloride. Colorless crystals, mp>240° C.

Example 14: 3-Acetyl-4-(2,4-difluorophenoxy) benzoylguanidine hydrochloride

14a)

1.0 eq. of methyl 3-acetyl-4-fluorobenzoate [preparation, see Example 12b)] was reacted, in DMF and in the presence of 1.1 eq. of $K_2CO_3$ and 1.3 eq. of 2,4-difluorophenol, to form methyl 3-acetyl-4-(2,4-difluorophenol)benzoate. Colorless crystals, mp 85°–87° C.

14b)

The methyl benzoate derivative from 14a) was hydrolyzed under standard conditions (MeOH/NaOH) and the resulting benzoic acid was converted into the guanidide in accordance with Variant A, and isolated as the hydrochloride. Colorless crystals, mp 188°–196° C.

Example 15: 3-Acetyl-4-(4-fluorophenoxy) benzoylguanidine hydrochloride

Was prepared in analogy with Example 14. Colorless crystals, mp 200°–210° C.

Example 16: 3-Acetyl-4-[2-(6-methyl) pyridylmethoxy]benzoylguanidine hydrochloride 16a)

1.2 eq. of trifluoromethanesulfonic anhydride were added, at −30° C., to 1 eq. of methyl 3-acetyl-4-hydroxybenzoate, 1.2 eq. of 2,6-dimethylpyridine and 0.2 eq. of DMAP in $CH_2Cl_2$, and the mixture was stirred at RT for 2 h. Adding a saturated solution of $NaHCO_3$, extracting by shaking three times with EA, drying over $MgSO_4$ and concentrating in vacuo yielded a yellow oil as the crude product. This was taken up in DMF, 1 eq. of 5-hydroxyquinoline and $K_2CO_3$ were added, and the mixture was heated to 120° C. After working up with a saturated solution of $NaHCO_3$/EA, purification was carried out using column chromatography. Methyl 3-acetyl-4-[2-(6-methyl)pyridylmethoxy]benzoate was isolated. MS (ES): 300 (M+1).

16b)

The benzoic ester derivative from 16a) was converted into the guanidide in accordance with Variant A. MS (ES): 327 (M+1).

Example 17: 3-Acetyl-5-methylsulfonylbenzoylguanidine hydrochloride

17a)

3-Bromobenzoic acid was converted into the corresponding 3-chlorosulfonic acid by treatment with chlorosulfonic acid. Subsequent hydrolysis, conversion into the disodium salt, and dimethylation with methyl iodide in DMF, resulted in methyl 5-bromo-3-methylsulfonylbenzoate. Crystals, mp 82°–85° C.

17b)

The benzoic ester derivative from 17a) was converted into methyl 3-acetyl-5-methylsulfonylbenzoate in analogy with Example 12a) and 12b). Colorless crystals, mp 106°–108° C.

17c)

The ester from 17b) was converted into the guanidide in accordance with Variant B, and subsequently isolated as the hydrochloride. Colorless crystals, mp 221°–223° C.

Example 18: 3-Acetyl-6-hydroxybenzoylguanidine hydrochloride 1.0 eq. of 3-acetyl-6-hydroxybenzoic acid was reacted with 1.1 eq. of carbonyldiimidazole and 5 eq. of guanidine in accordance with Variant A, and isolated as the hydrochloride. Colorless crystals, mp 170°–180° C.

Example 19: 3-Acetyl-5-bromo-4-hydroxybenzoylguanidine hydrochloride

19a)

Methyl 3-acetyl-4-hydroxybenzoate was reacted in chlorobenzene with 1.1 eq. of N-bromosuccinimide and a trace of AIBN to form methyl 3-acetyl-5-bromo-4-hydroxybenzoate. Colorless crystals, mp 106°–108° C.

19b)

The ester from 19a) was converted into the guanidide in accordance with Variant B, and isolated as the hydrochloride. Crystals, mp 230° C. with decomposition.

Example 20: 3-Acetyl-5-chloro-4-hydroxybenzoylguanidine hydrochloride

20a)

1 eq. of 4-acetoxy-3-chlorobenzoic acid was mixed with 3 eq. of $AlCl_3$, and the mixture was heated at 140° C. for 1 h. Working up with 2N HCl resulted in 3-acetyl-5-chloro-4-hydroxybenzoic acid. Yellow crystals, mp 226°–234° C.

20b)

The benzoic acid from 20a) was converted into the guanidide in accordance with Variant A, and isolated as the hydrochloride. Yellowish crystals, mp 198°–203° C.

Example 21: 3-Acetyl-5-bromo-4-methoxybenzoylguanidine hydrochloride

21a)

1 eq. of methyl 3-acetyl-5-bromo-4-hydroxybenzoate (preparation, see Example 19) was reacted, in acetone, with 2.0 eq. of $K_2CO_3$ and 2.1 eq. of methyl iodide to give methyl 3-acetyl-5-bromo-4-methoxybenzoate. Colorless oil, MS (ES): 288 (M+1).

21b)

The 4-methoxybenzoic ester from 21a) was hydrolyzed under standard conditions (MeOH/NaOH), and the resulting benzoic acid derivative was converted into the guanidide in accordance with Variant A, and isolated as the hydrochloride. Colorless crystals, mp 175°–178° C.

Example 22: 3-Acetyl-5-bromo-4-isopropoxybenzoylguanidine hydrochloride

Was prepared in analogy with Example 21. Colorless crystals, mp 158°–170° C.

Example 23: 3-Acetyl-5-bromo-4-benzyloxybenzoylguanidine hydrochloride

Was prepared in analogy with Example 21. Colorless crystals, mp 175°–182° C.

Example 24: 3-Acetyl-5-cyclopentyl-4-methoxybenzoylguanidine hydrochloride

24a)

Methyl 3-acetyl-5-bromo-4-methoxybenzoate was reacted, in accordance with Example 8b) and with mediation of $PdCl_2(dppf)$, with cyclopentylzinc chloride ($Br^-$ instead of $CF_3SO_3^-$ as the leaving group). Yellow oil, MS (ES): 277 (M+1).

24b)

The product from 24a) was hydrolyzed under standard conditions (MeOH/NaOH), and the resulting benzoic acid derivative was converted into the guanidide in accordance with Variant A, and isolated as the hydrochloride. Colorless oil, MS (ES): 304 (M+1).

Example 25: 3-Acetyl-4-(3-pyridinyl)-benzoylguanidine

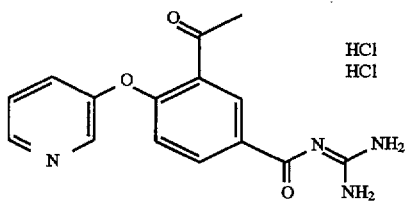

a) 5-Bromo-2-fluoro-acetophenone 4.1 g of 2-fluoroacetophenone are dissolved in 16 ml concentrated $H_2SO_4$ at room temperature and then 4.3 g dibromocyanuric acid, dissolved in in 24 ml of concentrated $H_2SO_4$, are added dropwise. The mixture was stirred for 1 h at RT. Then the mixture is poured on about 100 g of ice, and the solution is extracted 3× with 100 ml of $CH_2Cl_2$. Drying then takes place over $Na_2SO_4$ and the solvent is distilled off in vacuo. A brown oil results which is distilled in vacuo. boiling point 90° C. (1 Torr). After distillation 2.8 g of a colorless oil are obtained. MS (EI): 217 $(M+H)^+$ b) 3-Acetyl-4-fluoro-benzoic acid n-butylester 2.4 g of 5-bromo-2-fluoro-acetophenone, 5.2 ml of n-tributylamine, 70 mg of palladium(II)acetate and 1,3-bis (diphenylphosphino)propane are dissolved in 10 ml of n-butanol and 20 ml DMF, and the mixture was stirred 8 h at 100° C. under CO-atmosphere. The mixture is poured into 200 ml of a saturated aqueous solution of $NaHSO_4$, and the mixture is extracted 3 times with 100 ml MTB. Drying takes place over $Na_2SO_4$ and the solvent is removed in vacuo. Chromatography over kieselgel with MTB/DIP 1:1 affords 1,6 g of a colorless oil. $R_f$ (MTB/DIP 1:1)=0.38 MS (DCl): 239 $(M+H)^+$ c) 3-acetyl-4-(3-pyridinyl)-benzoic acid n-butylester 1.5 g of 3-acetyl-4-fluoro-benzoic acid n-butylester, 0.6 g of 3-hydroxypyridine and 4.1 g of $Cs_2CO_3$ are stirred in 20 ml of tetramethylurea for 2 h at 110° C. After cooling to RT the mixture is poured into 200 ml EE and the mixture is washed 3 times with 100 ml brine. Drying takes place over $Na_2SO_4$ and the solvent is distilled off in vacuo. Chromatography over silica gel with MTB furnishes 1.3 g of a pale yellow oil. $R_f$ (MTB)=0.30 MS (DCl): 314 $(M+H)^+$ d) 3-Acetyl-4-(3-pyridinyl)-benzoylguanidine 1.2 g of 3-acetyl-4-(3-pyridinyl)-benzoic acid n-butylester are converted into the guanidine in isopropanol in accordance with Variant B. Chromatography over silica gel with EE/MeOH 10:1 furnishes 360 mg of an amorphous solid. This solid is dissolved in 50 ml of 0.1N aqueous HCl-solution and the water and the HCl are removed in vacuo. The dihydrochloride is obtained. mp 165° C. (decomposition). $R_f$ (EE/MeOH 10:1)=0.15 MS (ES): 299 $(M+H)^+$

Pharmacological data

Inhibition of the $Na^+/H^+$ exchanger of rabbit erythrocytes

New Zealand White rabbits (Ivanovas) were given a standard diet containing 2% cholesterol for six weeks in order to activate $Na^+/H^+$ exchange and thus to be able to determine, by flame photometry, the influx of $Na^+$ into the erythrocytes by way of $Na^+/H^+$ exchange. The blood was removed from the aural arteries and rendered incoagulable with 25 IU of potassium heparin. A portion of each sample was used to determine the hematocrit in duplicate by centrifugation. Aliquots of 100 µl in each case were used for measuring the initial content of $Na^+$ in the erythrocytes.

In order to determine the amiloride-sensitive sodium influx, 100 µl of each blood sample were in each case incubated in 5 ml of a hyperosmolar salt/sucrose medium (mmol/l: 140 NaCl, 3 KCl, 150 sucrose, 0.1 ouabain, 20 tris-hydroxymethylaminomethane) at pH 7.4 and 37° C. After that, the erythrocytes were washed three times with ice-cold $MgCl_2$/ouabain solution (mmol/l: 112 $MgCl_2$, 0.1 ouabain), and hemolyzed in 2.0 ml of distilled water. The intracellular content of sodium was determined by flame photometry.

The net influx of $Na^+$ was calculated from the difference between the initial sodium values and the sodium content of the erythrocytes following incubation. The amiloride-inhibitable sodium influx was obtained from the difference in the sodium content of the erythrocytes following incubation with and without $3 \times 10^{-4}$ mol/l amiloride. The same procedure was used for the compounds according to the invention.

Results

Inhibition of the $Na^+/H^+$ exchanger:

| Example | $IC_{50}$ mol/l |
|---|---|
| 1 | $2.0 \times 10^{-6}$ |
| 2 | $1.0 \times 10^{-6}$ |
| 3 | $1.1 \times 10^{-6}$ |
| 4 | $1.2 \times 10^{-6}$ |

We claim:

1. A benzoylguanidine of the formula I

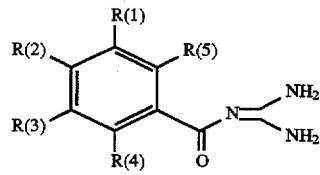

in which:

R(1) is R(6)—CO;

R(6) being $(C_1-C_8)$-alkyl, $(C_1-C_8)$-perfluoroalkyl, $(C_3-C_8)$-alkenyl or —$C_nH_{2n}$—R(9), n being zero, 1, 2, 3 or 4, R(9) being $(C_3-C_8)$-cycloalkyl, phenyl, biphenylyl or naphthyl, where the aromatic radicals are unsubstituted or substituted by 1–3 substituents selected from the group consisting of F, Cl, $CF_3$, methyl, methoxy and NR(10)R(11);

R(10) and R(11) being H, $(C_1-C_4)$-alkyl or $(C_1-C_4)$-perfluoroalkyl;

R(2) is H, F, Cl, Br, I, OH, CN, $NO_2$, $(C_1-C_8)$-alkyl, $(C_1-C_8)$-perfluoroalkyl, $(C_3-C_8)$-alkenyl or —$C_nH_{2n}$R (15);

n being zero, 1, 2, 3 or 4;

R(15) being $(C_3-C_8)$-cycloalkyl, phenyl, biphenylyl or naphthyl, where the aromatic radicals are unsubstituted or substituted by 1–3 substituents selected from the group consisting of F, Cl, $CF_3$, methyl, methoxy and NR(16)R(17);

R(16) and R(17) being H, $(C_1-C_4)$-alkyl or $(C_1-C_4)$-perfluoroalkyl;

or

R(2) is R(21)—$SO_m$ or R(22)R(23)N—$SO_2$—;

m being 1 or 2;

R(21) being $(C_1-C_8)$-alkyl, $(C_1-C_8)$-perfluoroalkyl, $(C_3-C_8)$-alkenyl or —$C_nH_{2n}$—R(24);

n being zero, 1, 2, 3 or 4;

R(24) being $(C_3-C_8)$-cycloalkyl, phenyl, biphenylyl or naphthyl; where the aromatic radicals are unsubstituted or substituted by 1–3 substituents selected from the group consisting of F, Cl, $CF_3$, methyl, methoxy and NR(27)R(28);

R(27) and R(28) being H, $(C_1-C_4)$-alkyl or $(C_1-C_4)$-perfluoroalkyl;

R(22) being H, $(C_1-C_8)$-alkyl, $(C_1-C_8)$-perfluoroalkyl, $(C_3-C_8)$-alkenyl or $-C_nH_{2n}-R(29)$, n being zero, 1, 2, 3 or 4;

R(29) being $(C_3-C_8)$-cycloalkyl, phenyl, biphenylyl or naphthyl, where the aromatic radicals are unsubstituted or substituted by 1–3 substituents selected from the group consisting of F, Cl, $CF_3$, methyl, methoxy and NR(30)R(31);

R(30) and R(31) being H, $(C_1-C_4)$-alkyl or $(C_1-C_4)$-perfluoroalkyl;

R(23) being H, $(C_1-C_4)$-alkyl or $(C_1-C_4)$-perfluoroalkyl;

or

R(2) is R(33)X—;

X is oxygen, S, NR(34) or (D=O)A—;

A being oxygen or NR(34);

D being C or SO;

R(33) being $(C_1-C_8)$-alkyl, $(C_3-C_8)$-alkenyl, $(CH_2)_bC_dF_{2d+1}$ or $-C_nH_{2n}-R(36)$;

b is zero or 1;

d is 1, 2, 3, 4, 5, 6 or 7;

n is zero, 1, 2, 3 or 4;

R(36) is $(C_3-C_8)$-cycloalkyl, phenyl, biphenylyl or naphthyl, where the aromatic radicals are unsubstituted or substituted by 1–3 substituents selected from the group consisting of F, Cl, $CF_3$, methyl, methoxy and NR(37)R(38);

R(37) and R(38) being H, $(C_1-C_4)$-alkyl or $(C_1-C_4)$-perfluoroalkyl;

R(34) being H, $CH_3$ or $CF_3$;

or

R(2) is —SR(40), —OR(40), —NHR(40), —NR(40)R(41), —CHR(40) R(42), —[CR(42)R(43)OH], —C≡CR(45), —CR(46)=CR(45) or —[CR(47)R(48)]$_u$—(CO)—[CR(49)R(50)]$_v$—R(44);

R(40) and R(41) are identical or different and are —(CH$_2$)$_p$—(CHOH)$_q$—(CH$_2$)$_r$—(CHOH)$_t$R(51) or —(CH$_2$)$_p$—O—(CH$_2$—CH$_2$O)$_q$—R(51);

R(51) is hydrogen or methyl;

u is 1, 2, 3 or 4;

v is zero, 1, 2, 3 or 4;

p, q and r are identical or different and are zero, 1, 2, 3 or 4;

t is 1, 2, 3 or 4;

R(42) and R(43) are identical or different and are hydrogen or $(C_1-C_6)$-alkyl or, together with the carbon atom carrying them, form a $(C_3-C_8)$-cycloalkyl;

R(44) is H, $(C_1-C_6)$-alkyl, $(C_3-C_8)$-cycloalkyl or —C$_e$H$_{2e}$—R(45);

e being zero, 1, 2, 3 or 4;

R(45) is phenyl, which is unsubstituted or substituted by 1–3 substituents selected from the group consisting of F, Cl, $CF_3$, methyl, methoxy and NR(52)R(53);

R(52) and R(53) being H or $(C_1-C_4)$-alkyl;

or

R(45) is $(C_1-C_6)$-alkyl which is unsubstituted or substituted by 1–3 OH;

R(46), R(47), R(48), R(49) and R(50) are hydrogen or methyl;

R(3) is defined as R(1) or R(2);

R(4) and R(5) are, independently of each other, defined as R(2);

and pharmaceutically tolerated salts thereof.

2. A compound of formula I as claimed in claim 1 in which:

R(1) is R(6)—CO;

R(6) being $(C_1-C_8)$-alkyl, $CF_3$ or $-C_nH_{2n}-R(9)$;

n being zero, 1, 2, 3 or 4;

R(9) being $(C_3-C_8)$-cycloalkyl or phenyl, where phenyl is unsubstituted or substituted by 1–3 substituents selected from the group consisting of F, Cl, $CF_3$, methyl, methoxy and NR(10)R(11);

R(10) and R(11) being H or $CH_3$;

R(2) is H, F, Cl, Br, I, OH, CN, $(C_1-C_8)$-alkyl, $CF_3$, $(C_3-C_8)$-alkenyl or $-C_nH_{2n}R(15)$;

n being zero, 1, 2, 3 or 4;

R(15) being $(C_3-C_8)$-cycloalkyl or phenyl, where phenyl is unsubstituted or substituted by 1–3 substituents selected from the group consisting of F, Cl, $CF_3$, methyl, methoxy and NR(16)R(17);

R(16) and R(17) being H or $CH_3$;

or

R(2) is R(21)—SO$_m$;

m being 2;

R(21) being $(C_1-C_8)$-alkyl, $CF_3$, $(C_3-C_8)$-alkenyl or $-C_nH_{2n}-R(24)$;

n being zero, 1, 2, 3 or 4;

R(24) being $(C_3-C_8)$-cycloalkyl or phenyl, which is unsubstituted or substituted by 1–3 substituents selected from the group consisting of F, Cl, $CF_3$, methyl, methoxy and NR(27)R(28);

R(27) and R(28) being H or $CH_3$;

or

R(2) is R(33)X—;

X is oxygen, S, NR(34) or (C=O)A—;

A being oxygen or NR(34);

R(33) being $(C_1-C_8)$-alkyl, $(CH_2)_bC_dF_{2d+1}$ or $-C_nH_{2n}-R(36)$;

b is zero or 1;

d is 1, 2, 3, 4, 5, 6 or 7;

n is zero or 1;

R(36) is $(C_3-C_8)$-cycloalkyl or phenyl, which is unsubstituted or substituted by 1–3 substituents selected from the group consisting of F, Cl, $CF_3$, methyl, methoxy and NR(37)R(38);

R(37) and R(38) being H or $CH_3$;

R(34) being H or $CH_3$;

R(3) is defined as R(1) or R(2);

R(4) and R(5) are, independently of each other, defined as R(2).

3. A compound of formula I as claimed in claim 1 in which:

R(1) is R(6)—CO;

R(6) being $(C_1-C_8)$-alkyl, $CF_3$ or $-C_nH_{2n}-R(9)$;

n being zero;

R(9) being $(C_3-C_8)$-cycloalkyl or phenyl, where phenyl is unsubstituted or substituted by 1–3 substituents selected from the group consisting of F, Cl, $CF_3$, methyl, methoxy and NR(10)R(11);

R4 R(10) and R(11) being H or $CH_3$;

R(2) is H, F, Cl, Br, I, OH, CN, $(C_1-C_8)$-alkyl, $CF_3$ or $-C_nH_{2n}R(15)$;

n being zero, 1 or 2;

R(15) being $(C_3–C_8)$-cycloalkyl or phenyl, where phenyl is unsubstituted or substituted by 1–3 substituents selected from the group consisting of F, Cl, $CF_3$, methyl, methoxy and NR(16)R(17);

R(16) and R(17) being H or $CH_3$;

or

R(2) is R(33)X—;

X is oxygen, S or NR(34);

R(33) is $(C_1–C_8)$-alkyl, $(CH_2)_b C_d F_{2d+1}$ or —$C_n H_{2n}$—R(36);

b is zero or 1;

d is 1, 2, 3 or 4;

n is zero or 1;

R(36) is phenyl, which is unsubstituted or substituted by 1–3 substituents selected from the group consisting of F, Cl, $CF_3$, methyl, methoxy and NR(37)R(38);

R(37) and R(38) being H or $CH_3$;

R(34) being $CH_3$;

R(3) is defined as R(1) or is H, F, Cl, Br, I, OH, $(C_1–C_8)$-alkyl, $CF_3$ or —$C_n H_{2n}$R(15);

n being zero, 1 or 2;

R(15) being $(C_3–C_8)$-cycloalkyl or phenyl, which is unsubstituted or substituted by 1–3 substituents selected from the group consisting of F, Cl, $CF_3$, methyl, methoxy and NR(16)R(17);

R(16) and R(17) being H or $CH_3$;

or

R(3) is R(21)—$SO_m$;

m being 2;

R(21) being $(C_1–C_4)$-alkyl or $CF_3$;

R(4) and R(5) are, independently of each other, hydrogen, F, Cl, OH, $CH_3$, $CF_3$, OMe, $OCF_3$, OH or $NH_2$.

4. A compound of formula I as claimed in claim 1 in which:

R(1) is R(6)—CO;

R(6) being $(C_1–C_2)$-alkyl or —$C_n H_{2n}$—R(9);

n being zero;

R(9) being phenyl, where phenyl is unsubstituted or substituted by 1–3 substituents selected from the group consisting of F, Cl, $CF_3$, methyl, methoxy and NR(10)R(11);

R(10) and R(11) being H or $CH_3$;

R(2) is H, F, Cl, Br, I, OH, $(C_1–C_8)$-alkyl or —$C_n H_{2n}$R(15);

n being zero, 1 or 2;

R(15) being $(C_3–C_8)$-cycloalkyl or phenyl, where phenyl is unsubstituted or substituted by 1–3 substituents selected from the group consisting of F, Cl, $CF_3$, methyl, methoxy and NR(16)R(17);

R(16) and R(17) being H or $CH_3$;

or

R(2) is R(33)X—;

X is oxygen;

R(33) is $(C_1–C_8)$-alkyl or —$C_n H_{2n}$—R(36);

n is zero or 1;

R(36) is phenyl, which is unsubstituted or substituted by 1–3 substituents selected from the group consisting of F, Cl, $CF_3$, methyl, methoxy and NR(37)R(38);

R(37) and R(38) being H or $CH_3$;

R(3) is H, F, Cl, Br, I or —$C_n H_{2n}$R(15);

n being zero, 1 or 2;

R(15) being $(C_3–C_8)$-cycloalkyl or phenyl, which is unsubstituted or substituted by 1–3 substituents selected from the group consisting of F, Cl, $CF_3$, methyl, methoxy and NR(16)R(17);

R(16) and R(17) being H or $CH_3$;

or

R(3) is R(21)—$SO_m$;

m being 2;

R(21) being $(C_1–C_4)$-alkyl;

R(4) and R(5) are, independently of each other, hydrogen, F, Cl, OH, $CH_3$, $CF_3$, OMe, $OCF_3$, OH or $NH_2$.

5. A process for preparing a compound I as claimed in claim 1, wherein a compound of the formula II

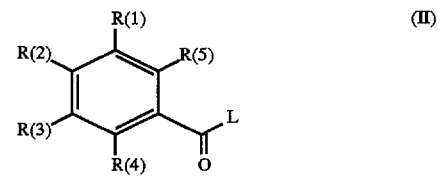

in which R(1) to R(5) have the meaning given in claim 1 and L is a leaving group which can readily be substituted by a nucleophile, is reacted with guanidine.

6. A pharmaceutical composition for treating arrhythmias, which comprises an effective amount for said treatment of a compound of formula I as claimed in claim 1 together with a pharmaceutically acceptable carrier.

7. A method for treating or preventing diseases caused by ischemic conditions, which comprises administering to a host in need of said treatment an effective amount of a compound of the formula I as claimed in claim 1.

8. A diagnostic agent for inhibiting the $Na^+/H^+$ exchanger and diagnosing hypertension and proliferative disorders, which comprises an effective amount for said inhibiting and diagnosing of a compound of the formula I as claimed in claim 1.

9. A pharmaceutical composition for treating myocardial infarction, angina pectoris, ischemic conditions of the heart, of the peripheral and central nervous systems, of the peripheral organs and limbs, of stroke and of conditions of shock, which comprises an effective amount for said treatment of a compound of formula I as claimed in claim 1 together with a pharmaceutically acceptable carrier.

10. A pharmaceutical composition for treating diseases caused by ischemic conditions, which comprises an effective amount of a compound of formula I or a salt thereof as claimed in claim 1 together with a pharmaceutically acceptable carrier.

* * * * *